United States Patent
Lee et al.

(10) Patent No.: US 8,013,202 B2
(45) Date of Patent: Sep. 6, 2011

(54) METHOD FOR SEPARATING AROMATIC COMPOUNDS USING SIMULATED MOVING BED OPERATION

(75) Inventors: Jin-Suk Lee, Seoul (KR); Nam-Cheol Shin, Chungcheongnam-do (KR)

(73) Assignee: Samsung Total Petrochemicals Co., Ltd., Dokgod-RI, Daesan-Up Seonsan-shi, Chungcheongnam-do (KR)

( * ) Notice: Subject to any disclaimer, the term of this patent is extended or adjusted under 35 U.S.C. 154(b) by 381 days.

(21) Appl. No.: 12/392,488

(22) Filed: Feb. 25, 2009

(65) Prior Publication Data
US 2009/0234170 A1    Sep. 17, 2009

(30) Foreign Application Priority Data

Mar. 13, 2008    (KR) .................. 10-2008-0023297

(51) Int. Cl.
*C07C 7/12*    (2006.01)
(52) U.S. Cl. ........................... 585/828; 585/820
(58) Field of Classification Search ............ None
See application file for complete search history.

(56) References Cited

U.S. PATENT DOCUMENTS

| | | | |
|---|---|---|---|
| 2008/0149565 A1* | 6/2008 | Lee et al. ............ | 210/663 |
| 2009/0069612 A1* | 3/2009 | Hotier et al. .......... | 585/470 |
| 2010/0125163 A1* | 5/2010 | Porter et al. ......... | 585/822 |
| 2010/0145119 A1* | 6/2010 | Lee et al. ............ | 585/323 |

OTHER PUBLICATIONS

UOP LLC, "Aromatics and Derivatives 'Parex Process'", UOP 2699C-14 899AD1M, 1999 UOP LLC, 25 East Algonquin Road, Des Plaines, IL 60017.
UOP LLC, "Aromatics and Derivatives 'PX-Plus Process'", UOP 2699C-13 899AD1N, 1999 UOP LLC, 25 East Algonquin Road, Des Plaines, IL 60017.

* cited by examiner

*Primary Examiner* — Tam M Nguyen
(74) *Attorney, Agent, or Firm* — Barlow, Josephs & Holmes, Ltd.

(57) ABSTRACT

Disclosed is a method for separating aromatic compounds using a simulated moving bed (SMB) operation, characterized by injecting each raw material having a different composition into each different part of an adsorption chamber so as to improve the recovery rate. More specifically, the present invention provides a method for separating aromatic compounds for improving p-xylene separation in a p-xylene separation process, by injecting a high p-xylene mixture from selective toluene disproportionation process (STDP) and low p-xylene mixture from other processes (for example, processes of reformer, isomerization reactor and transalkylation of aromatics having 9 carbon atoms) into each different part of an adsorption chamber.

4 Claims, 7 Drawing Sheets

METHOD FOR SEPARATING AROMATIC COMPOUNDS USING SIMULATED MOVING BED OPERATION

FOREIGN PRIORITY AND INCORPORATION BY REFERENCE

This Application claims the benefit of foreign priority under 35 USC §119 (b) of Korean Patent Application 10-2008-0023297, filed Mar. 13, 2008, the entire content of which is hereby incorporated by reference.

FIELD OF THE INVENTION

The present invention relates to a method for separating aromatic compounds using a simulated moving bed (SMB) operation. Specifically, it relates to a method for separating aromatic compounds characterized by separately injecting a mixture comprising p-xylene in high concentration (hereinafter, 'a high p-xylene mixture') and a mixture comprising p-xylene in low concentration (hereinafter, 'a low p-xylene mixture') into each different part of an adsorption chamber for p-xylene separation.

BACKGROUND OF THE INVENTION

Figure 1:
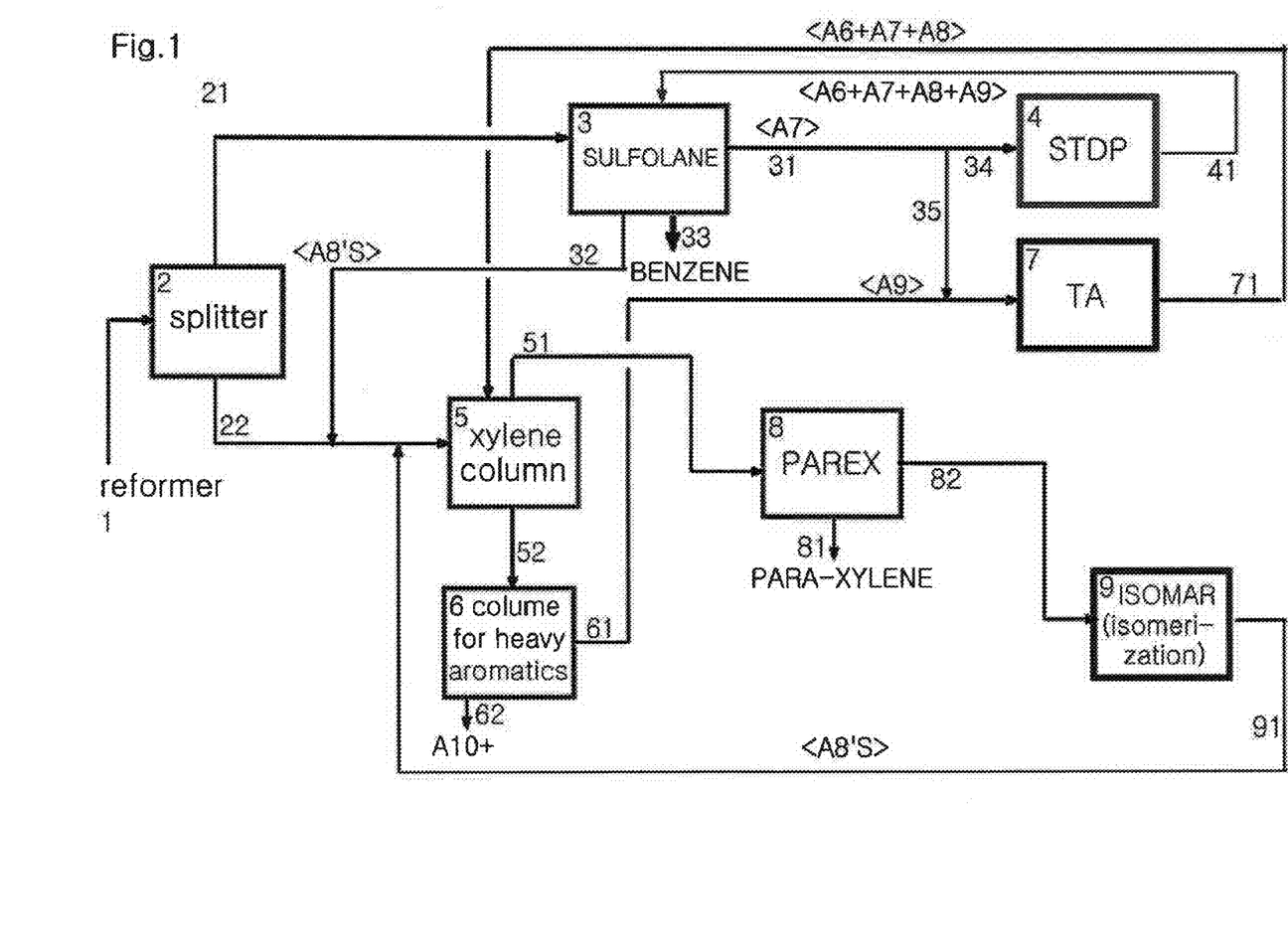
FIG. 1 is a schematic flow chart of a typical aromatic compound separation process in prior art.

Aromatic compound treatment processes (hereinafter, also referred as "aromatic compound separation processes") refer to processes for obtaining p-xylene (PX) and benzene (BZ) as major final products by treating a raw material, naphtha, in petrochemical plants. In a conventional aromatic compound separation process as represented in FIG. 1, the fundamental process wherein a xylene mixture containing one of major products, p-xylene (PX) is produced, includes 4 sub-processes: a reformer process; a xylene isomerization process; a transalkylation and disproportionation process of aromatic compounds having 7 carbon atoms as well 9 carbon atoms; and a selective toluene disproportionation (STDP) process of aromatic compounds having 7 carbon atoms.

In the conventional aromatic compound processes, the amount of p-xylene in the xylene mixture produced from the selective toluene disproportionation process reaches nearly 90 wt % (% by weight). In the meantime, the p-xylene fraction in the xylene mixture produced from other three processes does not get over the reaction equilibrium, being only about 20-24 wt %, owing to intrinsic characteristics of each particular process. Further, conventional processes also need to be improved in terms of productivity, since they cannot realize the optimal operation of an adsorption chamber, by injecting the xylene mixtures from the 4 sub-processes into the same single part of an adsorption chamber for p-xylene separation through only one inlet.

TECHNICAL PROBLEM

The present invention has been designed to solve the problems of prior arts as described above. The object of the invention is to provide a method for separating aromatic compounds using SMB operation for adsorptive separation, which provides remarkably improved p-xylene productivity (recovery rate) on the whole, by injecting a high p-xylene mixture and a low p-xylene mixture into each different part of an adsorption chamber, respectively, instead of mixing feeds having different composition and injecting the mixture into the same single part of the chamber for p-xylene separation.

SYMBOLS

SULFOLANE: process of benzene-toluene fractionation and removal of non-aromatics PAREX: p-xylene separation process ISOMAR: xylene isomerization process STDP: selective toluene disproportionation process Transalkylation: transalkylation of aromatics having 9 carbon atoms A6: aromatics having 6 carbon atoms A7: aromatics having 7 carbon atoms A8: aromatics having 8 carbon atoms A9: aromatics having 9 carbon atoms A10+: aromatics having 10 or more carbon atoms PX: p-xylene MX: m-xylene OX: o-xylene EB: ethylbenzene TOL: toluene

NARO: mixture of non-aromatics

PDEB: resulted product of ethylene benzene

DETAILED DESCRIPTION OF THE PREFERRED EMBODIMENT

In order to achieve the object as said above, the present invention provides a method for separating aromatic compounds using SMB operation for adsorptive separation, wherein the method comprises SULFORANE process for fractionating benzene/toluene and removing a non-aromatic compound, selective toluene disproportionation process, transalkylation process, xylene isomerization process, and p-xylene separation process; and is characterized by separately injecting a high p-xylene mixture from the selective toluene disproportionation process and low p-xylene mixtures from other processes into each different part of an adsorption chamber.

In the method for separating aromatic compounds according to the present invention, a selective toluene disproportionation reaction which is a major reaction in the selective toluene disproportionation process can be represented by the following reaction scheme:

(wherein R is a methyl group)

In the above reaction scheme, N refers to the number of moles of converted toluene. When a catalyst discharges reaction products through the open pores thereof, it restricts the diffusion rate of o-xylene and m-xylene at the time of discharge, resulting in selective discharge of a desired product, p-xylene. The selective discharge of p-xylene may be schematically represented as below:

As for a catalyst that can selectively disproportionate toluene, thus selectively discharging p-xylene, for example, a catalyst used in PX-Plus process from UOP may be used.

The product resulted from the selective toluene disproportionation, i.e. a high p-xylene mixture preferably contains 85-95 wt % of p-xylene, 3-8 wt % of m-xylene, 1-4 wt % of ethylbenzene, and 0.5-1 wt % of o-xylene.

In the transalkylation process in the method for separating aromatic compounds according to the present invention, a mixture of aromatic compounds which contains p-xylene is obtained from transalkylation of toluene and aromatic compounds of 9 carbon atoms. Transalkylation of toluene and aromatic compounds of 9 carbon atoms such as trimethylbenzene, i.e. the major reaction occurred in the transalkylation process can be represented by the following reaction scheme:

As for a catalyst for transalkylation of toluene and aromatic compounds of 9 carbon atoms such as trimethyl benzene, thus producing a mixture of aromatic compounds which contains p-xylene, for example, a catalyst used in TAC 9 process from UOP may be used.

In the xylene isomerization process in the method for separating aromatic compounds according to the present invention, a xylene mixture (a mixture mostly comprised of m-xylene and o-xylene) is isomerized such that m-xylene and o-xylene at the amount which can achieve reaction equilibrium are converted to p-xylene, and the reaction scheme is as follows:

As for such catalyst for the isomerization process, for example, a catalyst used in ISOMAR process from UOP may be used.

The method for separating aromatic compounds of the present invention is characterized by injecting a high p-xylene mixture from the selective toluene disproportionation process and a low p-xylene mixture which contains about 20-24 wt % of p-xylene, from other processes (for example, such as the xylene isomerization process, the translalkylation and the like) into each different part of an adsorption chamber, respectively. Preferably, the high p-xylene mixture may be further subjected to benzene/toluene/xylene separation process (BTX separation process), and then the xylene mixture resulted therefrom may also be used as the high p-xylene mixture.

As for the p-xylene separation process in the method for separating aromatic compounds according to the present invention, commercially available SMB methods (Parex process of UOP, Eluxyl process of IFP) and crystallization method may also be used. Recently, there are some cases where both of the methods are suitably combined for use.

Figure 2:
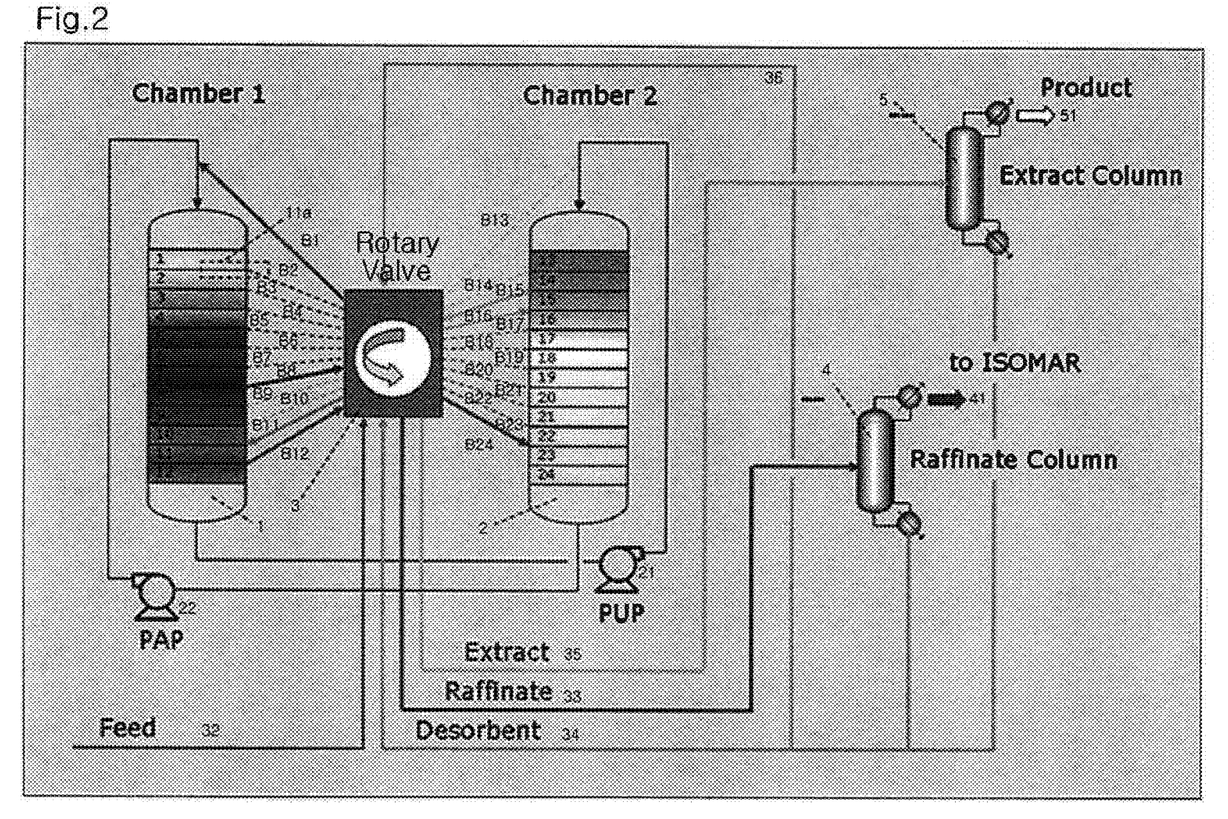
FIG. 2 is a schematic view of Parex process.

FIG. 2 illustrates a schematic view of Parex process that is a p-xylene separation process.

As it has been illustrated in FIG. 2, in Parex process, layers of multiple beds which are filled with adsorbents are formed in the adsorption chambers 1, 2. Each bed in the adsorption chambers 1, 2 is connected to a rotary valve 3 by a multiple access lines B1-B24. The number of beds is typically 12 per chamber, thus 24 in total.

The rotary valve 3 of Parex process connects three inlet ports such as a fluid feed inlet port 32, a desorbent inlet port 34, and a secondary flush inlet port 36 and two outlet ports such as a raffinate outlet port 33 and an extract outlet port 35 to the multiple access lines B1-B24, respectively. The detailed structure of the rotary valve 3 is well known to a person who has ordinary knowledge in the art to which the present invention belongs.

The raffinate column 4 of Parex process separates raffinate drawn from the raffinate outlet port 33, by a first separator, and then returns a part of the separated raffinate, as a desorbent, to a desorbent inlet port 34.

The extract column 5 of Parex process separates the extract drawn from the extract outlet port 35, by a second separator, and then returns a part of the separated extract, as a desorbent, to a desorbent inlet port 34.

In an adsorption separation process using simulated moving bed such as Parex process, a stationary phase does not flow in practical. When changing the location of each port for desorbent, extract, fluid feed, raffinate, secondary flush, line flush in, and line flush out toward the flow direction of the mobile phase at an interval of a certain switching time, the column is relatively placed opposite to the flow direction of the mobile phase centering around each port. By doing so, an imaginary stationary phase flow can be achieved so that it is possible to simulate the countercurrent flow to a mobile phase. Adsorbents being used as a stationary phase are filled in the beds.

Although the location of each port 32, 33, 34, 35 for said desorbent, extract, fluid feed and raffinate cannot be moved in continuous way, similar effects can be obtained by installing multiple access lines B1-B24 as shown in FIG. 2 and then periodically moving each flow to the neighboring line at an interval of a certain switching time via rotary valve 3. Therefore, among feeds injected through a fluid feed inlet port 32, materials having weak adsorptiveness come out together with the mobile phase through a raffinate outlet port 33, and materials having strong adsorptiveness are adsorbed on the adsorbent in each bed B1-B24 of adsorption chambers 1, 2 and come out from the column through an extract outlet port 35 owing to the relative movement of the column made at a certain switching time.

In Parex process, input of a feed and a desorbent, and discharge of an extract and a raffinate are carried out through the same single pipeline by nature of the process. The multiple access lines B1-B24 that are the pipelines connecting an adsorption chamber with a rotary valve are present as many as the number of beds in the adsorption chamber, thus being referred as a bed line. According to a SMB operation procedure, a certain pipeline is used for introducing a feed (in FIG. 2, B1 line is used for this purpose), and after an elapse of a certain period, then used for discharging a final product. At this time, the initial portion of the final product discharged during the switching time is discharged together with the feed which has been filled in the pipeline, thereby rather deteriorating the purity of the final product. In order to prevent such problem, procedures such as, so-called, a line flush and a secondary flush are additionally carried out. The line flush is a procedure for washing the inside of the pipeline by drawing a small amount of liquid in the adsorption chamber from a bed right below the bed into which desorbent is injected (in FIG. 2, B12 line is used for this purpose) and again returning it to the inside of the adsorption chamber through the pipeline used for injection of the feed (in FIG. 2, B23 line is used for this purpose). The liquid used in the line flush procedure is not pure desorbent, containing a small amount of different liquid components. Therefore, a secondary flush procedure for washing the pipeline again, is further added. The secondary flush is a procedure to finally wash the inside of the pipeline by injecting pure desorbent into an adsorption chamber through a corresponding pipeline just before discharging the final product (In FIG. 2, B16 line is used for this purpose). These flushing strategies are used on the premise that they do not cause any side effects, since desorbent by nature is easily separated, even though it is mixed with the extract, during the course of a distillation process carried out before obtaining final products.

Among each bed line in FIG. 2, the solid lines with an arrow represent bed lines currently in use, and the dotted lines without an arrow represent bed lines currently not in use. Color of each bed line means different species of liquid filled in the bed line.

Figure 3:
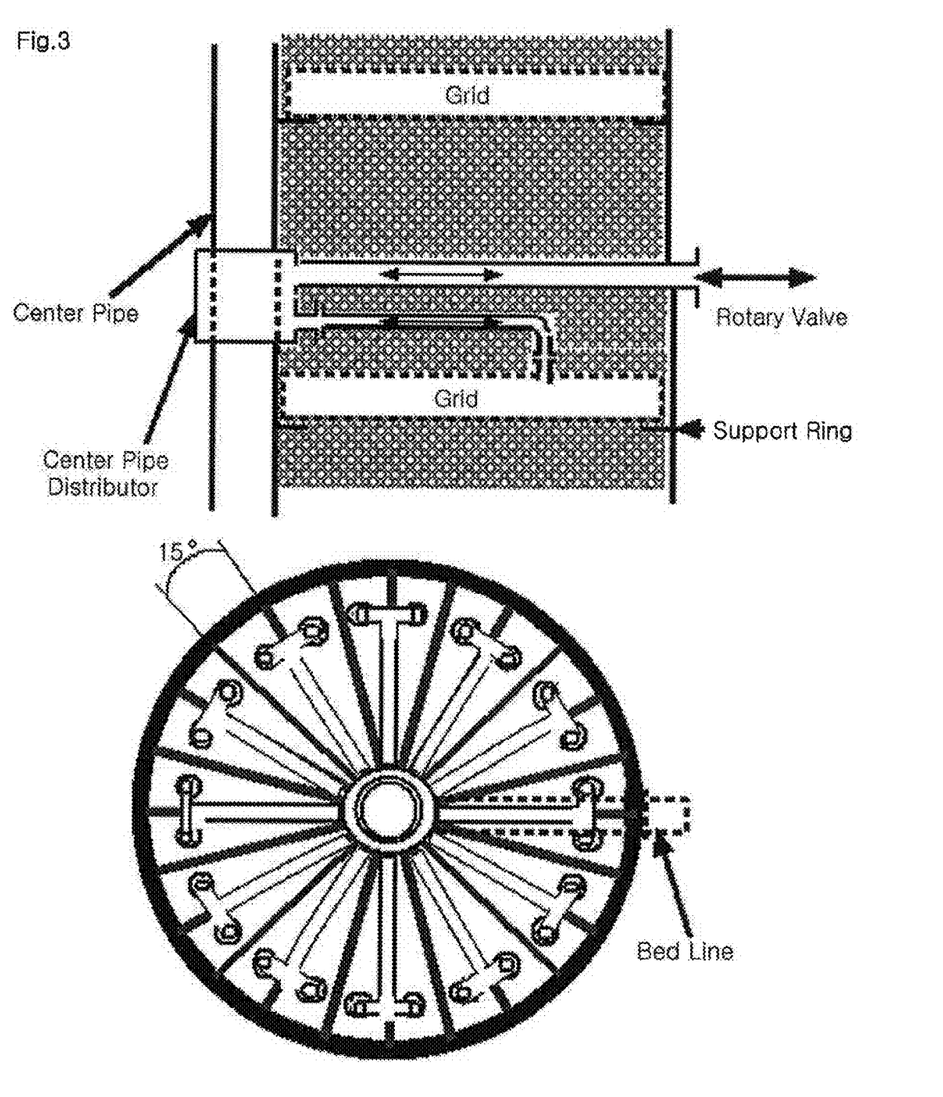
FIG. 3 is a grid-structure view of an adsorption chamber.

PX separation process by using SMB operation periodically controls the opening and closing of a valve placed on each step of a multistep adsorption chamber, thereby resulting an effect as if an adsorbent and a fluid contact each other in countercurrent. By doing so, it effectively separates, xylene isomers in continuous way. Each bed is separated by grids that are specially manufactured for making the flow distribution of liquid uniform, as schematically represented in FIG. 3. The grid is formed by double screens which allow only fluid to pass therethrough, thereby being served as a partition of an adsorption bed. 24 pieces of pie-shaped grids form one bed. The bed line that is a passage of feed, is also a channel for coming in and out of a fluid inside the adsorption chamber, and connects the adsorption chamber and a rotary valve, as being connected between the double screens of a grid.

Figure 4:
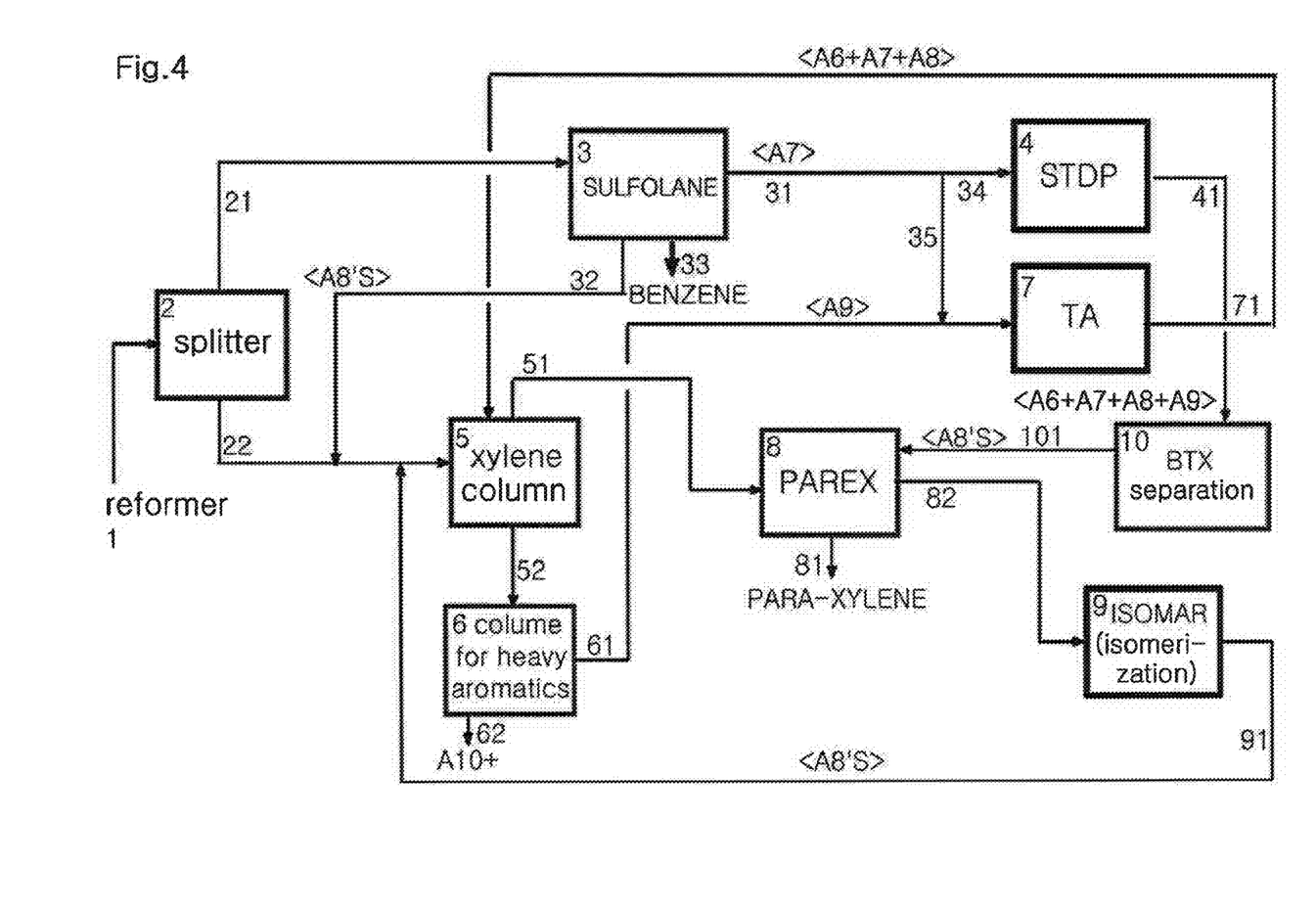
FIG. 4 is a schematic flow chart illustrating one embodiment of an improved process for separating aromatic compounds according to the present invention.

In FIG. 4, a schematic view illustrating a preferred embodiment of an improved process for treating aromatic compounds, according to the present invention is represented. Hereinafter, the method for separating aromatic compounds according to the present invention is further described in detail with referring to FIG. 4.

Referring to FIG. 4, a feed mixture (reformate) of aromatic compounds inputted from a reformer 1 to a splitter 2 is separated into a mixture containing aromatic compounds having 6 and 7 carbon atoms, i.e. benzene and toluene, and another mixture of rather heavier aromatic compounds, for example such as xylene having 8 carbon atoms, wherein the former is subjected, through a line 21, into SULFORANE process 3 wherein benzene/toluene fractionation and a non-aromatic compound removing process are carried out, and the latter is subjected, through a line 22, into a xylene column 5. In SULFORANE process, the mixture of benzene and toluene is separated into each benzene and toluene, wherein benzene is discharged through a line 33, and toluene is inputted into STDP process 4 (Selective Toluene Disproportionation) and transalkylation process 7 through a line 34 and a line 35. The mixture resulted from the selective disproportionation in STDP process 4, comprises benzene A6, toluene A7, xylene A8 and aromatic compounds A9 having 9 carbon atoms such as trimethylbenzene. Particularly, among them, it contains p-xylene at the amount of about 85-95 wt %. The mixture resulted from STDP process 4 is inputted into BTX separation process 10 through a line 41, wherein xylene having 8 carbon atoms is separated from lighter or heavier components such as trimethylbenzene, and inputted into F2 position (see FIG. 6) of PAREX process 8 through a line 101. The xylene mixture inputted into PAREX process 8 through a line 51 is separated into p-xylene and other xylene mixtures, wherein the former is discharged through a line 81 and the latter is discharged through a line 82 and inputted into ISOMAR process 9, that is a xylene isomerization process. Xylene having 8 carbon atoms discharged from SULFOLANE process 3 is inputted together with trimethylbenzene that is heavier than the xylene having 8 carbon atoms into a xylene column 5, wherein aromatic compounds having 9 or more carbon atoms are discharged through a line 52 and inputted to a column 6 for heavy aromatic compounds, and the xylene mixture having 8 carbon atoms is discharged through a line 51 and inputted into F1 position (See FIG. 6) of PAREX process 8 that is a p-xylene separation process. The xylene mixture inputted to PAREX process 8 through the line 51 is separated into p-xylene and a mixture of other types of xylene, wherein the former is discharged through a line 81, and the latter is discharged through a line 82 and inputted into a xylene isomerization process, ISOMAR process 9. The resulted product of ISOMAR process 9 is discharged through a line 91 and again inputted into the xylene column 5. The mixture of aromatic compounds having 9 or more carbon atoms inputted into the column 6 for heavy aromatic compounds via the line 52, is separated into a mixture of aromatic compounds having 9 carbon atoms including trimethylbenzene A9 and aromatic compounds having 10 or more carbon atoms A10+ in the column 6, wherein the former is inputted into transalkylation (TA) process 7 through a line 61 and the latter is discharged through a line 62. The aromatic compounds having 9 carbon atoms inputted into the transalkylation process 7 go under the reaction of transalkylation with toluene inputted from SULFORANE process 3 through a line 31 in the transalkylation process 7, resulting a product comprising p-xylene. The resulted product is again inputted into the xylene column 5 through a line 71.

ADVANTAGEOUS EFFECT

By the method for separating aromatic compounds according to the present invention, productivity of p-xylene can be remarkably improved, as compared to conventional methods.

MODE FOR INVENTION

Hereinafter, the present invention is further illustrated in detail, through the following examples and comparative examples. However, these examples by no means limit the scope of the present invention.

According to the process illustrated in FIG. 4, p-xylene separation process was carried out.

The initial raw material, Naphtha was desulfurized and inputted into a reformer 1, from which a mixture of aromatic compounds (reformate) was discharged. The reformate from the reformer 1 was inputted into a splitter 2, at the rate of 176 t/h. After that, in p-xylene separation process 8, a high p-xylene mixture (having 85-90 wt % of p-xylene) discharged from benzene/toluene/xylene separation process 10 wherein a mixture from STDP process 4 was treated, and a low p-xylene mixture from a xylene column 5 were inputted into each different part of an adsorption chamber so as to carry out p-xylene separation.

Figure 5:
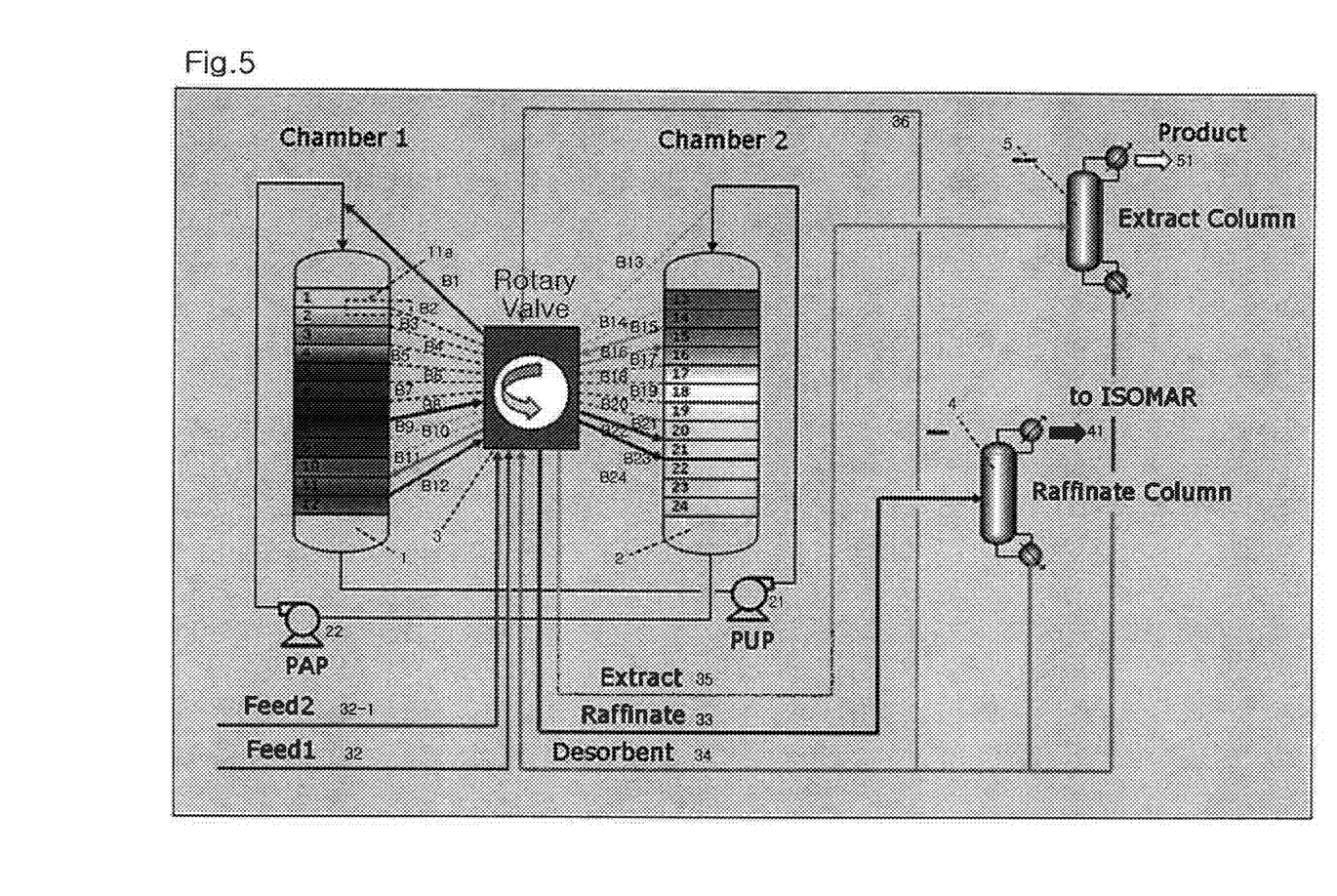
FIG. 5 is a schematic view of an improved Parex process according to the present invention.

At this time, the p-xylene separation process wherein two feeds are inputted into each different part of the adsorption chamber was conducted as illustrated in FIG. 5. Specifically, the low p-xylene mixture (feed 1) from the xylene column 5 was inputted into a conventional injection position for single feed (see, FIG. 6). In the meantime, the high p-xylene mixture (feed 2) from STDP process 4 was injected at a position 3 beds nearer to the extract outlet as compared to the injection position of the low p-xylene mixture (see, FIG. 6). Correspondingly, the line flush inlet was adjusted to be placed 2 beds nearer to the extract outlet as compared to the conventional position.

Table 1 represents the specific flow rate and composition of each feed of Examples according to the present invention and Comparative example according to prior arts. In the two examples, the total amount of each component being inputted was same.

TABLE 1

| operation mode | feed | flow rate of feed (m³/h) | composition (%) | | | | |
|---|---|---|---|---|---|---|---|
| | | | p-xylene | m-xylene | o-xylene | ethylbenzene | toluene |
| comparative example (single injection) | feed | 361.152 | 27.1119 | 46.52326 | 21.57151 | 4.480314 | 0.213015 |
| Examples (double injection) | feed 1 (low concentration) | 327.203712 | 20.95022 | 50.60316 | 23.67474 | 4.457521 | 0.214365 |
| | feed 2 (high concentration) | 33.948288 | 86.5 | 7.2 | 1.3 | 4.7 | 0.2 |

For comparing the performances of Examples and Comparative example, "SIMBAS Model" (manufactured by Samsung total) which can simulate Parex process, was used. Since SIMBAS Model is a simulating device that is based on physicochemical model well corresponding to the commercial Parex operation conditions, it is considered that it can be suitably used for estimating the effects of changes in operation strategies as in the present invention.

Figure 6:
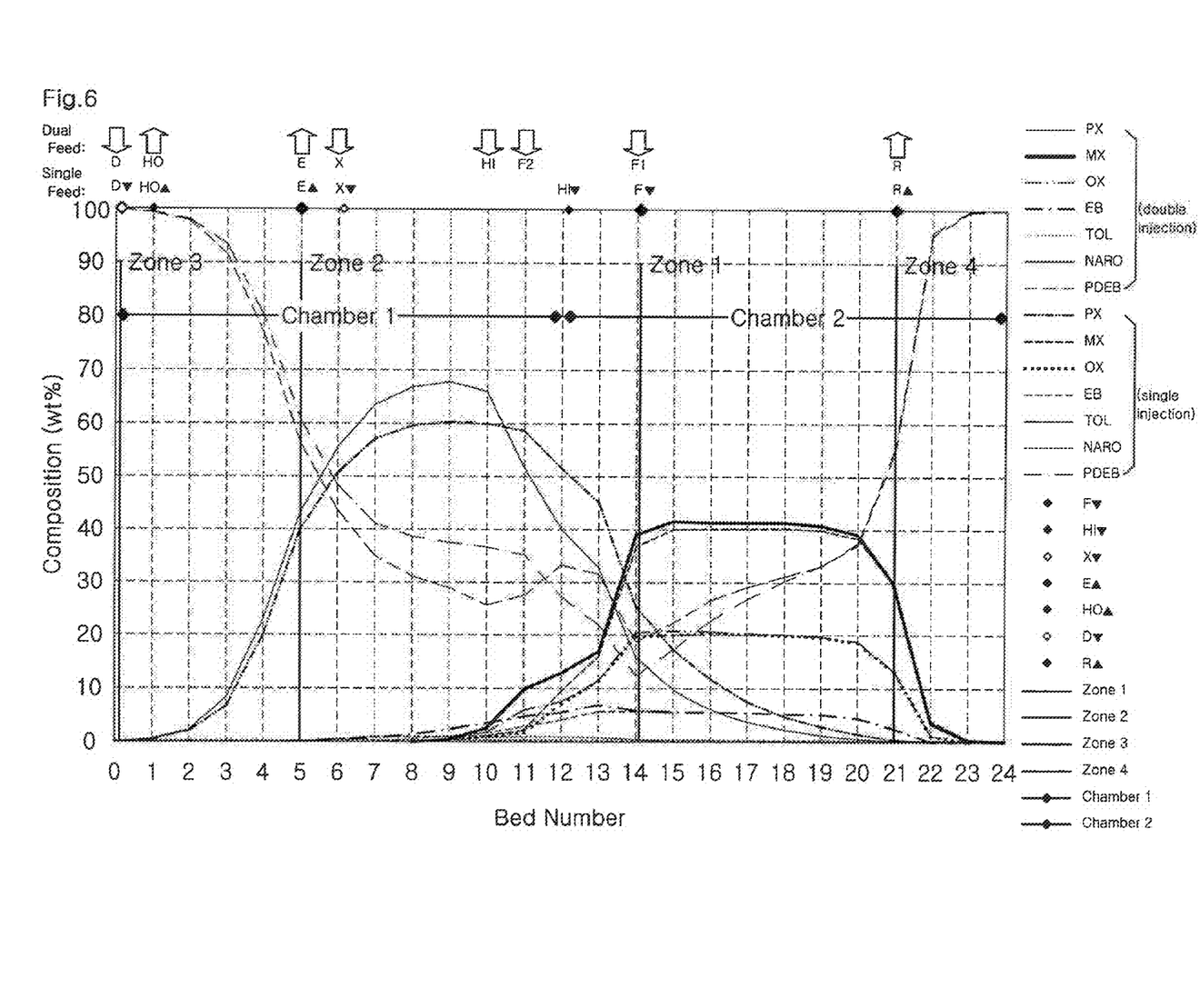
FIG. 6 is a graphic view comparing the concentration distributions of each component from the improved Parex process according to the present invention and conventional Parex process.
Figure 7:
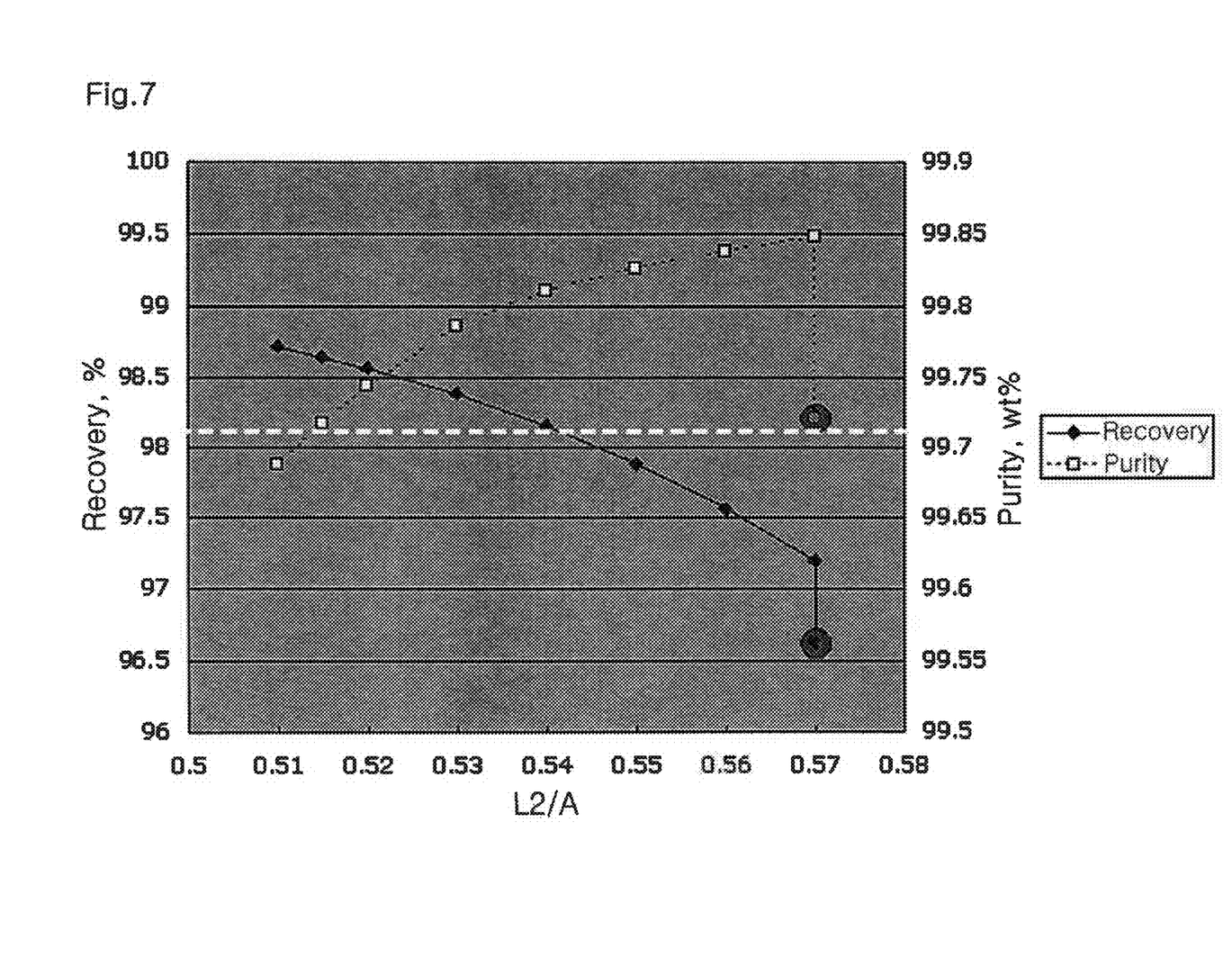
FIG. 7 is a graphic view showing the progress of the effect of increasing recovery rate in improved Parex process according to the present invention.

In FIG. 6, the concentration distributions of each component assayed along the axis direction of an adsorption chamber was illustrated, in each case. FIG. 7 is a view illustrating the changes in recovery rate and product purity, wherein the recovery rate is represented as a function of L2/A (one of representative operation parameters in Parex operation) which is one of major operation parameters, in the same flow rate at the time of injection of each case. When maintaining the purity, it was found that L2/A could be lowered from 0.57 to 0.515, and the recovery rate could be improved from 96.64% to 98.65%. Assuming that yearly production capacity of p-xylene is 600 thousands tons, the above percentage means that 12,000 tons or more per annum could be further produced.

What is claimed is:

1. A method for separating aromatic compounds using a simulated moving bed (SMB) operation, which comprises SULFORANE process that is a benzene/toluene fractionation and a non-aromatic compound removing process; selective toluene disproportionation process; transalkylation process; xylene isomerization process; and p-xylene separation process, characterized by separately injecting a high p-xylene mixture from the selective toluene disproportionation process and a low p-xylene mixture from other processes into each different part of an adsorption chamber in the p-xylene separation process.

2. The method according to claim 1, wherein the concentration of p-xylene in the high p-xylene mixture is in the range of 85-95 wt %.

3. The method according to claim 1, wherein the concentration of p-xylene in the low p-xylene mixture is in the range of 20-24 wt %.

4. The method according to claim 2, wherein the concentration of p-xylene in the low p-xylene mixture is in the range of 20-24 wt %.

* * * * *